(12) United States Patent
Patel et al.

(10) Patent No.: US 7,273,840 B2
(45) Date of Patent: Sep. 25, 2007

(54) METHOD FOR PROVIDING DILUTION THICKENING USING POLYDEXTROSE BASED BIPHASIC COMPOSITIONS

(75) Inventors: Rajesh Patel, Middlebury, CT (US); Kavssery Parameswaran Ananthapadmanabhan, Highland Mills, NY (US); Lin Yang, Fort Lee, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 111 days.

(21) Appl. No.: 11/181,010

(22) Filed: Jul. 14, 2005

(65) Prior Publication Data

US 2007/0015682 A1 Jan. 18, 2007

(51) Int. Cl.
*C11D 1/00* (2006.01)
*C11D 3/22* (2006.01)
*C11D 3/37* (2006.01)
*C11D 17/00* (2006.01)

(52) U.S. Cl. ............... 510/417; 510/340; 510/421; 510/426; 510/470; 510/473; 510/474; 510/535; 510/537

(58) Field of Classification Search ............... 510/340, 510/421, 426, 470, 473, 474, 535, 537, 417
See application file for complete search history.

(56) References Cited

U.S. PATENT DOCUMENTS

| 3,718,609 | A | 2/1973 | Weimer | |
| 3,810,470 | A | 5/1974 | Von Gunten | |
| 5,906,973 | A | 5/1999 | Ouzounis et al. | |
| 6,429,177 | B1 | 8/2002 | Williams et al. | |
| 6,727,209 | B2 * | 4/2004 | Pereira et al. | 510/130 |
| 6,787,511 | B2 * | 9/2004 | Patel et al. | 510/130 |
| 2004/0033914 | A1 * | 2/2004 | Patel et al. | 510/130 |
| 2004/0038837 | A1 * | 2/2004 | Pereira et al. | 510/130 |

FOREIGN PATENT DOCUMENTS

| CA | 2211313 | 2/1998 |
| DE | 195 04 192 A1 | 8/1996 |
| WO | 94/28108 | 12/1994 |
| WO | 2005-016304 A1 | 2/2005 |

* cited by examiner

*Primary Examiner*—Brian Mruk
(74) *Attorney, Agent, or Firm*—Ronald A. Koatz

(57) ABSTRACT

The invention provides methods for obtaining dilution thickening behavior. Specifically, polydextrose induced biphasic compositions have been unexpectedly found to induce such behavior.

3 Claims, 3 Drawing Sheets

METHOD FOR PROVIDING DILUTION THICKENING USING POLYDEXTROSE BASED BIPHASIC COMPOSITIONS

FIELD OF THE INVENTION

The present invention relates to methods for providing dilution thickening behavior, particularly using polydextrose based biphasic compositions.

BACKGROUND

The concept of dilution thickening describes a phenomenon whereas the formulation thickens upon dilution with solvent, typically water. Therefore, a formulation is thin enough to get in and out of a container, but becomes sufficiently thick to retain on the hand or skin during application when water is added.

Typically, a dilution thickening composition is one in which a surfactant system has been thickened (e.g., to enhance viscosity) through use of salt (see Canadian Patent No. 2,211,313). Typically in such compositions, a so-called peak viscosity is achieved when salt is first added, and further addition of salt leads to viscosity reduction ("oversalting"). When the composition is diluted, the "oversalted" composition increases in viscosity in the process referred to as "dilution thickening"

Separately from the above phenomenon, the use of so-called "biphasic liquids" is known in the art. These are defined by the fact that the liquid is divided into two phases. Most of these liquids comprise both one layer which is an aqueous layer and a second layer comprising a water immiscible oily liquid (see U.S. Pat. No. 3,718,609 to Weimer; and U.S. Pat. No. 3,810,470 to Olson, Jr. et al., for example).

Biphasic compositions comprising an upper and lower aqueous phase are disclosed in U.S. Pat. No. 6,429,177 to Williams. The compositions comprise (a) 5 to 35% surfactant; (b) 1 to 12% thickener; (c) 4 to 20% polyalkylene glycol and (d) sufficient non-chelating mineral salt (typically "at least 4% or greater) to induce phase separation.

A particular biphasic is one that may be induced by addition of a sufficient quantity of specifically defined polydextrose. Such biphasic is defined, for example, in U.S. Pat. No. 6,787,511 to Patel et al.

BRIEF DESCRIPTION OF THE INVENTION

Figure 1:
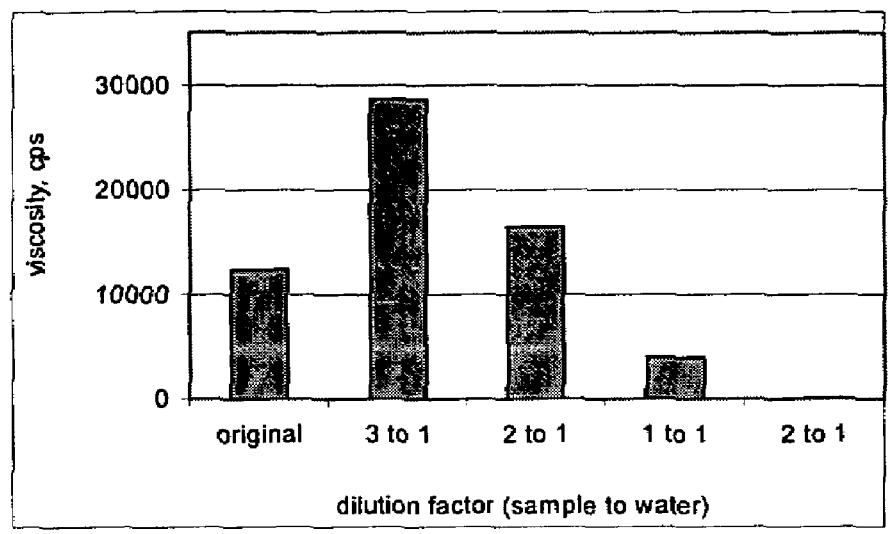
FIG. 1 is a graph of viscosity changes of sample solution (2:1 sodium lauryl ether sulfate to cocoamidopropyl betaine) when diluted in water at various ratios.

Unexpectedly, applicants have found that the specific polydextrose induced biphasics have dilution thickening ability; and that this effect is obtained with use of little or no salt.

Specifically, the invention relates to a method of providing dilution thickening using compositions comprising (1) 5% to 75%, preferably 6% to 40% by wt. of a surfactant selected from the group consisting of anionic surfactants, nonionic surfactants, amphoteric/zwitterionic surfactants, cationic surfactants and mixtures thereof;

(2) at least 15%, more preferably at least 20% by wt. of polydextrose or mixture of polydextrose molecules, wherein the degree of polymerization (e.g., number of linking glucose units) is 4 to 22 (this corresponds to MW of about 600 to about 3600); and (3) balance water and minors.

In general, salt is not required for the noted dilution thickening effect. However, if it is desired to achieve dilution thickening at lower levels of total sugar and surfactant, salt may be added. For example, in one embodiment of the claims, the compositions may comprise at least 1% salt and levels of polydextrose may be 10% (assuming there is sufficient surfactant to achieve dilution thickening effect at 10% sugar and 1% salt). Further, the invention may comprise compositions wherein at least 2% salt is used and polydextrose level may be as low as 5% (again, assuming there is enough surfactant). In general, as levels of surfactant and sugar are increased, less salt is needed.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The invention relates to novel methods for providing dilution thickening behavior. In particular, the invention relates to use of polydextrose based biphasic compositions to provide dilution thickening. The effect is accomplished using compositions comprising little or no salt. Salt is not required, but allows for use of less overall sugar and/or surfactant if this is desired.

As indicated above, dilution thickening is a phenomenon used, in part, to ensure that viscosity of given composition is thin enough to be poured from a container yet, when the product is used, it will thicken and accordingly enhance retention (e.g., of oils and/or other emollients) on the skin.

Unexpectedly, applicants have found that polydextrose based biphasics, such as the type disclosed in U.S. Pat. No. 6,787,511 (hereby incorporated by reference into the subject application), provide the desired dilution thickening behavior using little or no salt.

In particular, when sample is diluted so that it is at ratio of about 1.5:1 (sample to water), preferably about 2:1 and higher (up to limit where there is no dilution at all), it will thicken; and, as ratio of water rises, eventually the formula will thin and dilute for rapid rinsing.

The compositions which will provide dilution thickening comprise as noted below.
 (1) 5% to 75% by wt. of a surfactant selected from the group consisting of anionic surfactant, nonionic surfactants, amphoteric/zwitterionic, cationic surfactant and mixtures thereof;
 (2) at least 15% polydextrose, wherein the degree of polymerization (i.e., number of linking glucose units) is 4 to 22 or have an MW of 600 to 3600; preferably MW is 700 to 1800, more preferably 900 to 1500 and more preferably 900 to 1200; and
 (3) balance water and minors.

In these compositions, when sufficient amount of specified polydextrose is added, phase separation occurs. For example, this is shown in the Examples wherein, when 20% polydextrose MD180 (MW 1000) is added, separation occurs. Different surfactant systems can be used and the specific type of surfactants is not a limiting factor.

The compositions may be used in combination with a transparent package in order to view the liquid. Thus, in one embodiment, the invention also comprises a system comprising said transparent or translucent package in combination with the liquid.

Typically, once the biphasic composition is formed (e.g., the composition "settles" after having been shaken), the viscosity of the lower layer is lower than that of the upper layer.

Also, the density of lower layer is typically greater than that of upper layer.

Typically, in such biphasic liquids, there is no recrystallization visible after composition has been standing for 6 months at room temperature.

The final product will have shower-gel like viscosity of 100 to 5000 mPas, preferably 200 to 4000 at shear rate $10s^{-1}$ at 25° C. measured using Haake RV20 Rotovisco Rheometer.

In a another embodiment of the invention, a small amount of salt is used and the amount of polydextrose needed to induce biphasic liquid is reduced. More specifically, in this embodiment, the composition comprises at least 1% salt and at least 10% polydextrose.

In a third embodiment, the composition comprises at least 2% salt and at least 5% polydextrose.

The various components of the composition are discussed in greater detail below.

Surfactant

The surfactant generally will comprise 5 to 75% by wt. of the total composition.

The surfactant is a surfactant which may be selected from the group consisting of anionic surfactants, nonionic surfactants, amphoteric/zwitterionic surfactants, cationic surfactants and mixtures thereof. Preferably, there will be at least one anionic surfactant.

Non-limiting examples of anionic surfactants are disclosed in McCutcheon's *Detergents and Emulsifiers*, North American Edition (1986), published by Allured Publishing Corporation; McCutcheon's *Functional* materials, North Americas Edition (1992), both of which are incorporated by reference into the subject application.

Examples of anionic surfactants include sarcosinates, sulfates, isethionates, glycinates, taurates, phosphates, lactylates, glutamates and mixtures thereof. Among isethionates are preferred alkoxyl isethionates such as sodium cocoyl isethionate, sodium lauroyl isethionate and mixtures.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium, magnesium and triethanolamine. Another suitable class of anionic surfactants are the water-soluble salts of the organic, sulfuric acid reaction products of the general formula:

$$R_1\text{—}SO_3\text{—}M$$

wherein $R_1$ is chosen from the group consisting of a straight or branched chain, saturated aliphatic hydrocarbon of radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and 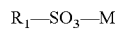-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts or ammonium or triethanolamine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853.

Other useful anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further non-limiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Non-limiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are alkylamino carboxylates such as glutamates, especially those having carbon chains between $C_8$ and $C_{16}$. Non-limiting examples of glutamates include ammonium, sodium, potassium and alkanolamine (e.g., triethanolamine) salts of lauroyl glutamate, myristoyl glutamate, and cocoyl glutamate.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures therefor.

Especially preferred for use herein is ammonium lauryl sulfate, ammonium lauryl ether sulfate, sodium lauryl ether sulfate, sodium lauroyl sarcosinate, sodium cocoyl sarcosinate, sodium myristoyl sarcosinate, sodium lauroyl lactate, and triethanolamine lauroyl lactylates.

Nonionic Lathering Surfactants

Non-limiting examples of nonionic lathering surfactants for use in the compositions of the present invention are disclosed in McCutcheon's, *Detergents and Emulsifiers*, North American Edition (1986), published by allured Published Corporation; and McCutcheon's, *Functional materials*, North American Edition (1992); both of which are incorporated by reference herein in their entirety.

Nonionic lathering surfactants useful herein include those selected form the group consisting of alkyl glucosides, alkyl polyglucosides, polyhydroxy fatty acid amides, alkoxylated fatty acid esters, alcohol ethoxylates, lathering sucrose esters, amine oxides, and mixtures thereof.

Alkyl glucosides and alkylipolyglucosides are useful herein, and can be broadly defined as condensation articles of long chain alcohols, e.g., C8-30 alcohols, with sugars or starches or sugar or starch polymers i.e., glycosides or polyglycosides. These compounds can be represented by the formula $(S)_n$—O—R wherein S is a sugar moiety such as glucose, fructose, mannose, and galactose; is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein $R^1$ is H, $C_1$-$C_4$ alkyl, 2-hydroxyethyl, 2-hydroxypropyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polyhydroxy hydrocarbyl moiety having a linear hydrocarbyl chain with at least 3 hydroxyl directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. As especially preferred surfactant corresponding to the above structure is coconut alkyl N-methyl glucoside amide (i.e., wherein the $R^2CO$-moiety is derived form coconut oil fatty acids). Processes for making compositions containing polyhydroxy fatty acid amides are disclosed, for example, in GB Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798 to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxyl alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyidi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, diemethylhexadecyclamine oxide.

Non-limiting examples of preferred nonionic surfactants for use herein are those selected form the group consisting of C8-C14 glucose amides, C8-C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, *Detergents and Emulsifiers*, North American Edition (1986), published by Allured Publishing Corporation; and McCutcheon's, *Functional Materials*, North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonaine 16SP from Lonza Corp.), lauryl bis-(2-hydroxyethyl) carboxymethyl betaine, oleyl dimethyl gamma-carboxypropyl betaine, lauryl bis-(hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Example of sultaines and hydroxysultaines include materials such as cocamidopropyl hydroxysultaine (available as Mirataine CBS from Rhone-Poulenc).

Preferred for use herein are amphoteric surfactants having the following structure:

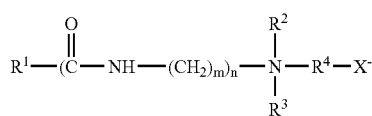

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are CH$_3$; X is selected form the group consisting of CO$_2$, SO$_3$ and SO$_4$; $R^4$ is selected form the group consisting of saturated or unsaturated, straight or branched chain alkyl, unsubstituted or mono-substituted with hydroxy, having from 1 to about 5 carbon atoms. When X is CO$_2$, $R^4$ preferably has 1 to 3 carbon atoms, more preferably 1 carbon atom. When X is SO$_3$ or SO4, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine);

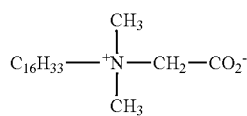

Cocamidopropylbetaine

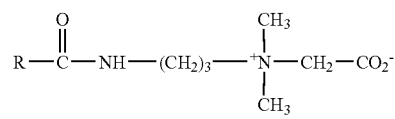

Cocamidopropyl Hydroxy Sultaine
wherein R has from about 9 to about 13 carbon atoms

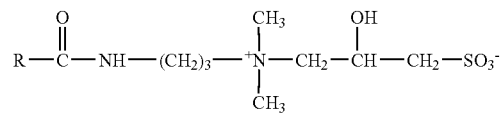

wherein R has from about 9 to about 13 carbon atoms.

Cationic Surfactants

Cationic surfactants are another useful class of surfactants that can be employed as auxiliary agents. They are particularly useful as additives to enhance skin feel, and provide skin conditioning benefits. One class of cationic surfactants is heterocyclic ammonium salts such as cetyl or stearyl pyridinium chloride, alkyl amidoethyl pyrrylinodium methyl sulfate, lapyrium chloride.

Tetra alkyl ammonium salts is another useful class of cationic surfactants. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides; behenyl dimethy ammonium chloride.

Other types of cationic surfactants that can be employed are the various ethoxylated quaternary amines and ester quats. Examples are PEG-5 stearyl ammonium lactate (e.g., Genamin KSL manufactured by Clarion), PEG-2 coco ammonium chloride, PEG-15 hydrogenated tallow ammonium chloride, PEG 15 stearyl ammonium chloride, dialmitoyl ethyl methyl ammonium chloride, dipalmitoyl hydroxyethyl methyl sulfate, strearyl amidopropyl dimethylamine lactate.

Still other useful cationic surfactants are quaternized hydrolysates of silk, wheat, and keratin proteins.

Polydextrose

The compound which added to the formulation which induces formation of biphasic (multiphasic) liquid is polydextrose. Generally, the polydextrose has a formulation as follows:

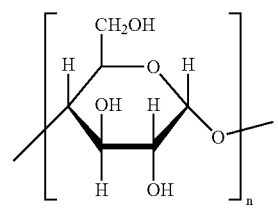

wherein n (defining number of linking glucose units) is from about 4 to about 22.

The biphasic inducing polydextrose compounds of the invention may also be defined by molecular weight in that they should have MW range of from 600 to about 3600, more preferably 700 to 3000, more preferably 700 to 1800, more preferably 900 to 1500.

Whether defined by glucose units or MW, it should be understood that the critical point is that the structure is such as to induce formation of a multiphasic/biphasic formulation defined by those characteristics which in turn define the biphasic liquid (e.g., viscosity of and stability in the biphasic state).

One source of polydextrose are corn sweeteners. Corn sweeteners are a class of sweeteners derived from corn by hydrolyzing corn starch polymers down into dextrose units of various lengths. The degree of conversion of the starch molecule is measured by the dextrose equivalent, D. E., corn sweeteners are more highly converted and have lower molecular weights. Depending on the degree of conversion of the starch molecule, corn sweeteners are classified as follows:

very low conversion: 20 D.E. and lower;
low conversion: 20-38 D.E.;
regular conversion: 38-48 D.E.;
intermediate conversion: 48-58 D.E.;
high conversion: 58-68 D.E.;
extra high conversion: 68 D.E. and higher.

The degree of conversion affects the functionality of the corn sweetener, lower D.E. corn sweeteners have a greater effect on increasing the glass transition temperature of their mixtures with sugars. An important class of corn sweeteners in this regard are the maltodextrins, hydrolyzed from starch to a D.E. of less than 20. A comprehensive series of maltodextrins are manufactured by the Grain Processing Corporation under the tradename Maltrin.

The amount of polydextrose used to induce biphasic state may vary depending on whether salt/electrolyte is used.

Thus, for example, if no salt is used (use of no or little salt also distinguishes this invention from other biphasic liquids of the art where relatively large amounts of salt, e.g., greater than 3% by wt., are in fact required to induce the biphasic liquid), then there is generally needed at least 15% by wt. of polydextrose to induce biphasic separation (assuming a surfactant concentration of at least 20%). If some salt is added (e.g., at least 0.5%, preferably at least 1.0%), the amount of polydextrose needed goes down to 10% by wt. (assuming there is enough surfactant). If at least 2% salt is used, the amount of polydextrose may be 5% (again, assuming there is enough surfactant).

It should be noted that there is an interplay between total surfactant plus sugar; and the amount of salt needed. As total amount of surfactant plus sugar increases, less salt, if any, is needed for dilution thickening effect.

There is also generally a balance between amount of surfactant used and amount of polydextrose. Generally lower surfactant requires more polydextrose and, conversely, more surfactant requires less polydextrose. Thus, for example, 5% to 10% by wt. surfactant may require about 40% or more polydextrose and 35% surfactant may need only about 10-15% polydextrose, even in the absence of salt. The various permutations for a typical composition may be seen, for example, in the phase diagram of FIG. 2, where the boundary between one layer and two layer is seen.

Generally, the upper limit of polydextrose used is about 75%. This is not an upper limit with regard to inducing biphasic liquid.

If electrolyte/salt is used, it typically will be used in amount of 0.5% to no higher than 4%, preferably no higher than about 3% by wt., more preferably 2.5% or less, more preferably 2.0 or less of total composition.

Preferably, the electrolyte is not a chelating electrolyte (these are generally poor in biodegradability).

Typically, the electrolyte should be a salt of a sulphate, bisulfate, carbonate, bicarbonate, phosphate, chloride, etc. Examples include sodium sulphate, potassium sulphate, ammonium sulphate, sodium chloride, and magnesium chloride. Magnesium sulphate and sodium chloride are particularly preferred.

Finally, the balance of composition is water and minors.

To measure the dilution thickening effect of sugar, surfactant etc., dilution is typically measured at a formulation to water ratio of 90:10 to 10:90, preferably 85:15 to 15:85, more preferably 80:20 to 20:80.

Optional

The following optional ingredients may be used in the multiphasic/biphasic compositions of the invention.

The composition may contain polyalkylene glycol. The polyalkylene glycol should be an alcohol, glycol or polyether of minimal molecular weight which is not irritating to the skin.

Examples of such include alcohols, particularly polyalkylene oxides having MW 200-6000, preferably 200 to 3000. The polyalkylene glycol can be comprised of ethylene oxide, propylene oxide, butylene oxide or their mixtures either as polymers or copolymers. Specific examples include polyethylene glycols such as PEG 400. As noted, use of such alcohols is not required.

The composition may further comprise thickeners. Generally, the thickener/viscosity modifier serves to thicken the upper and/or lower layer.

Thickeners which may be used include hydrophobically modified polyethers. Examples of this class of thickeners which may be used include but are not limited to sugar esters such as PEG (160) sorbitan triisostearate (Rheodol TWS-399C ex Kao Chemicals) or PEG-120 Pentaerythrityl Tetrastearate ex Croda. Other examples include Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt); and Carbopol® polymers from Noveon.

Another class of suitable polymers are hydrophobically modified cellulose ethers including but not limited to hydroxyethyl cellulose, hydroxypropylcellulose and cellulose ethers with long pendant chains such as nonoxynyl hydroxyethylcellulose (Amerchol Polymer HM 1500).

Another class of suitable polymers are the hydrophobically modified acrylate copolymers such as Antil 208® (ex Goldschmidt) (acrylate/steareth-50 acrylate copolymer).

Another class of suitable polymers are the hydrophobically modified polyurethanes such as Acrysol series (e.g., Acrysol RM-2020) from Rhom and Haas.

Another class of suitable thickeners are xanthan gums, guar gums and chemically modified guar gums.

In addition to the ingredients noted above, the compositions of the invention may contain hydrotropes including but not limited to short chain monohydric or dihydric alcohols, xylene sulphonate and hexylene glycol whose purpose is to avoid the formation of liquid crystal phases resulting from the separation of the surfactant material into the upper phase hence increasing its apparent concentration.

The compositions may comprise benefit agents. Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, polyols (e.g., saccharides), enzyme and α- or β-hydroxy acid either alone or entrapped in an oily benefit agent.

The benefit agent may be found in either the upper or the lower layer depending on its solubility and partition coefficient, for example, oil may partition into the upper layer while more water soluble agents (e.g., $^s$x-hydroxyacids) may go into the lower.

The compositions may comprise perfumes, sequestering agents such as EDTA EHDP in amounts 0.01 to 1%, preferably 0.01 to 0.05%; coloring agents, opacifiers and pearlizers such as zinc stearate, magnesium stearate, TiO2, mica, EGMS (ethylene glycol monostrearate) or styrene/acrylate copolymers.

The compositions may further comprise antimicrobials such as 2-hydroxy 4,2'4' trichlorodiphenylether (DP300), 3,4,4'-trichlorocarbanilide, essential oils and preservatives such as dimethyl hydantoin (Glydant XL 1000), parabens, sorbic acid etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used including Quatrisoft LM-200 Polyquaternium-24, Merquat Plus 3330- Polyquaternium 39; and Jaguar® type conditioners.

Composition may also include clays such as Bentonite® claims as well as particulates such as abrasives, glitter, and shimmer.

The compositions of the invention, when unmixed, have a viscosity of the lower layer which is lower than the viscosity of the upper layer and a density of the lower layer which is greater than the density of the upper layer.

The compositions of the invention, in a separated state, are also stable in that no recrystallization (e.g., in the lower layer) occurs even when left sitting for more than 6 months at temperature of 0° C.

Compositions of the invention have an experiential element in that they are intended to be agitated by the consumer to mix and form a single visible phase before separating again after a time, anywhere from about a few seconds to not more than about 24 hours.

When mixed, the compositions have a viscosity in the range of 100 to 5000, preferably 200-400 mPas at a shear rate of $10s^{-1}$ at 25° C. at a shear rate of $10\ s^{-1}$ at 25° C., as measured by using Haake RV20 Rotivisco Rheometer.

Finally, the packages in which the compositions are contained are translucent or transparent. By this is meant that the materials (e.g., plastics) have a light transmittance of greater than 50%, preferably greater than 75%, more preferably greater than 85% as measured at wavelength of 460 nm as determined by standard spectroscopy method. In practical terms the package should be sufficiently transparent to permit the separation of the two or more layers to be visible to the naked eye.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

Methodology:

Measurement Of Viscosity

Description

Haake Rheometer was used to measure the viscosities of liquid and semisolid personal wash products in the small scale with the viscosity measured at various shear rates.

Equipment

The instrument was an RV 20 Rotovisco RC 20 rheometer which includes a stand and sample temperature control unit, cups and bobs for loading the sample, a waterbath which is maintained at 25° C. and a computer and plotter to manipulate and record the data.

Operational Procedure

Haake rheometer, computer, monitor and printer were turned on.

Water bath: Waterbath was filled with water to a required level, the appropriate temperature was set and water bath was turned on.

Measurement Systems: Sample was loaded into rheometer and equilibrated to 25° C.

a) the appropriate cup and bob for the product are selected as noted below.
  i) NV for viscosity measurements of low viscous products, e.g. diluted solutions, fruit juices, etc;
  ii) SV1 for viscosity measurements of high viscosity liquids working in the low to medium range which consists of a SV cup with a rotor(bob). This is the cup and bob that is typically used to measure shower gel products;
b) the rotor(bob) was secured on to the top segment of the measuring system;
c) the RV 20 rheometer was adjusted using the zero button;
d) sample was poured into the cup until almost three fourths filled (approx. 20 g) and then the cup was carefully slid through the temperature controller and screwed to the main segment of the rheometer so that it was immersed in the product and sample was slightly above the rim of the bob;
e) waited 5 to 10 minutes after loading the sample to ensure equilibration of sample to set temperature (set parameters on computer while waiting for temperature equilibration).

Computer:

a) floppy disc was inserted and previous standard file was loaded if one is already saved on disc. If not, the following details were loaded into the computer:

i) measurement: select SV1, NV1, SV2P depending on the spindle used;
ii) select four segments for four shear rates, 1, 10, 100, 400 at 25° C. and in 10 steps;
b) on the computer screen follow the steps below to load the above details:

measurement—identification (record details of the sample);
measurement—parameter—select SV1;
measurement—go immediately (after sample is equilibrated);
c) this starts the measurement which takes about 10 minutes;
d) once the measurement was completed, results were saved on floppy disk; results were either printed or set as graphical representation.

Results

The results were recorded as viscosity in mPas (cps) at the shear rates: 1/sec, 10/sec and 100/sec. The temperature and spindle (bob) size were recorded with each sample measurement.

Materials & Methods

Materials

TABLE 2

Raw Materials

| | Trade Name | Structure |
|---|---|---|
| Na-Laureth Ether Sulfate | Steol C5-230 | — |
| Coco Amido Propyl Betaine | Tegobetaine F-50 | — |
| Almeo Blend | Almeo Blend | — |
| Sorbitol | Sorbitol | CH₂OH-HCOH-HOCH-HCOH-HCOH-CH₂OH |
| Sucrose | Sucrose | (sucrose structure) |
| Glucose | Glucose | (glucose structure) |
| Polydextrose (Av. MW = 3600) | Maltrine M40 | (polydextrose structure) |
| Polydextrose (Av. MW = 1800) | Maltrine M100 | |
| Polydextrose (Av. MW = 1000) | Maltrine M180 | |
| Polydextrose (Av. MW = 720) | Maltrine M250 | |
| Magnesium Sulfate | Mg*SO4 | — |

Formulation Preparation:

A simple surfactant solution was prepared at about 5 wt. % to about 35.0 wt. % without any saccharides. Then saccharides were added to desired level. After adding saccharides, sample was heated for 1 hour at 60° C. to dissolve any solid materials, then allowed to cool to room temperature. Once sample reached equilibrium at room temperature, it was mixed by shaking and observation are made.

Viscosity & Product Appearance

Formulations were screened for viscosity using standard PW protocols as set forth in methodology section above. The formulations were observed for any discoloration and re-crystallisation of saccharides at room temperature.

EXAMPLES

Example 1-6 and Comparative 1-4

Polydextose (i.e., Polydextrose M180) was examined for its ability to promote the formation of biphasic shower gel formulations, compared to sucrose, sorbitol and glucose. Results are set forth in Table 1 and 2 below.

TABLE 1

Sucrose, Sorbitol, Glucose and Polydextrose Comparison

| Ingredients | Comparative 1 % Ingredients | Comparative 2 % Ingredients | Comparative 3 % Ingredients | Example 1 % Ingredients | Example 2 % Ingredients |
|---|---|---|---|---|---|
| Na-Laureth Ether Sulfate | 10.0 | 10.0 | 10.0 | 10.0 | 8.3 |
| CocoAmido Propyl Betaine | 5.0 | 5.0 | 5.0 | 5.0 | 8.3 |
| Sucrose | 10-50 | — | — | — | — |
| Sorbitol | — | 10-50 | — | — | — |
| Glucode | — | — | 10-50 | — | — |
| Polydextrose M180 (avg MW = 1000) | — | — | — | 40.0 | 33.3 |
| MgSO4 | — | — | — | — | — |
| NaCl | — | — | — | — | — |
| PEG-400 | — | — | — | — | — |
| Water | Q.S to 100 | Q.S to 100 | Q.S to 100 | Q.S to 100 | Q.S to 100 |
| Biphasic | NO | NO | NO | Yes, Slight | Yes, 80:20 |

As seen from Table 1, when 15-16% surfactant is used (SLES/CAPB), only the polydextrose was able to promote phase separation in the absence of salt (Example 1 and 2)

In Table 2, shown below, applicants test for the effect of salt (e.g., MgSO$_4$) as well as for the effect of surfactant level versus amount of polydextrose needed.

TABLE 2

| Ingredients | Comparative 4 % Ingredients | Example 3 % Ingredients | Example 4 % Ingredients | Example 5 % Ingredients | Example 6 % Ingredients |
|---|---|---|---|---|---|
| Na-Laureth Ether Sulfate | 8.3-11.5 | 8.3-11.5 | 8.3 | 3.3 | 23.3 |
| CocoAmido Propyl Betaine | 8.3-11.5 | 8.3-11.5 | 8.2 | 1.7 | 11.7 |
| Polydextrose M040 (avg MW = 3600) | — | — | — | — | — |
| Polydextrose M100 (avg MW = 1800) | 23.0-35.0 | — | — | — | — |
| Polydextrose M180 (avg MW = 1000) | — | 23.0-35.0 | 20.0 | 60.0 | 15.0 |
| Polydextrose M250 9avg MW = 720) | — | — | — | — | — |
| MgSO4 | — | — | 1.0-3.0 | — | — |
| NaCl | — | — | — | — | — |
| PEG-400 | — | — | — | — | — |
| Water | Q.S to 100 | Q.S to 100 | Q.S to 100 | Q.S to 100 | Q.S to 100 |
| Biphasic | NO | Yes, 60:40 | Yes, 80:20 to 50:50 | Yes, 90:10 | Yes, 90:10 |

This Table also shows various points. First, this Table shows that the polydextrose level can be lowered without increasing surfactant level, if small amounts of salt (e.g., MgSO$_4$) are used (see Example 4). Also, Table 2 shows that higher levels of polydextrose permit much lower levels of surfactant (Example 5) and, conversely, high levels of surfactant permit use of lower levels of polydextrose (Example 6). One other interesting point is that polydextrose M100 does not appear to form biphasic. However, as seen in Table 3 below, when salt is added, biphasic is formed, even at lower surfactant levels.

Example 7-12 and Comparative 5

Different surfactant systems are also able to produce biphasic formulations when combined with the proper levels of polydextrose and salt. As with SLES/CAPB, the blend of ammonium laurylether sulfate, ammonium lauryl sulfate and cocoylmonoethanolamide will also promote phase separation (See Table 3 below). Examples 7-9 and Comparative 5 compare polydextrose M180 with and without salt in the surfactant mix. No phase separation is achieved with 25% polydextrose M180 alone (Comparative 5), but phase separation can be achieved with incorporation of low levels of MgSO$_4$ or NaCl (Formulations 7-9).

Also, the addition of low levels of salt promote phase separation with other polydextrose. Similar biphasic formulations can be produced with polydextrose M250 (Example 10), polydextrose M100 (Example 11) and polydextose M040, although the lower layer is turbid in these three formulations (Table 3 below). By using low levels of salt, a number of different polydextrose materials with different molecular weights and varying numbers of glucose units can be used to promote the formation of biphasic surfactant formulations.

TABLE 3

Surfactant Blend

| Ingredients | Comparative 5 % Ingredients | Example 7 % Ingredients | Example 8 % Ingredients | Example 9 % Ingredients | Example 10 % Ingredients | Example 11 % Ingredients | Example 12 % Ingredients |
|---|---|---|---|---|---|---|---|
| Na-Laureth Ether Sulfate | — | — | — | — | — | — | — |
| CocoAmido Propyl Betaine | 2.0 | 2.0 | 2.0 | 2.0 | 2.0 | 2.0 | 2.0 |
| Ammonium Lauryl Sulfate; Ammonium Laurylether Sulfate; Cocomono-ethanolamide | 13.0 | 13.0 | 13.0 | 13.0 | 13.0 | 10.0 | 10.0 |
| Polydextrose M040 (avg. MW = 3600) | — | — | — | — | — | — | 5.0 |
| Polydextrose M100 (avg MW = 1800) | — | — | — | — | — | 5.0 | — |
| Polydextrose M180 (avg MW = 1000) | 25.0 | 20.0 | 20.0 | 20.0 | — | — | — |
| Polydextrose M250 (avg MW = 720) | — | — | — | — | 20.0 | — | — |
| MgSO4 | 0.0 | 1.0 | 1.0 | — | — | — | — |
| NaCl | — | — | — | 1.5 | 3.0 | 3.0 | 3.0 |
| PEG-400 | — | — | 2.0 | — | — | — | — |
| Water | Q.S to 100 | Q.S to 100 | Q.S to 100 | Q.S to 100 | Q.S. to 100 | Q.S. to 100 | Q.S. to 100 |
| Biphasic | NO | Yes, 60:40 | Yes, 60:40 | Yes, 80:20 | Yes, 50:50 | Yes, 80:20 | Yes, 40:60 |

Examples 13 and 14 below are similar to Examples 11 and 12 except they use 5% salt instead of 3%.

| Ingredients | Example 13 % Ingredients | Example 14 % Ingredients |
|---|---|---|
| Na-Laureth Ether Sulfate | — | — |
| CocoAmido Propyl Betaine | 2.0 | 2.0 |
| Ammonium Lauryl Sulfate; Ammonium Laurylether Sulfate; Cocomonoethanolamide | 10.0 | 10.0 |
| Sucrose | — | — |
| Sorbitol | — | — |
| Glucode | — | — |
| Polydextrose M040 (avg. MW = 3600) | — | 5.0 |
| Polydextrose M100 (avg MW = 1800) | 5.0 | — |
| Polydextrose M180 (avg MW = 1000) | — | — |
| Polydextrose M250 (avg MW = 720) | — | — |
| MgSO4 | — | — |
| NaCl | 5.0 | 5.0 |
| PEG-400 | — | — |
| Water | Q.S to 100 | Q.S to 100 |
| Biphasic | Yes, 50:50 | Yes, 70:30 |

Example 15

Table 4 below shows a variety of formulation parameters that lead to biphasic product formulations as indicated in the Table below.

TABLE 4

Formulations parameters that lead to Biphasic product formations as indicated in the phase separation column.

| % Total Surfactant | % MD 180 | % MgSO4 | % Water | Phase Separation | Top (cm) | Bottom (cm) | % Top Layer |
|---|---|---|---|---|---|---|---|
| 15.0 | 10.0 | 1.00 | 74.0 | NO | — | — | |
| 14.3 | 14.3 | 0.95 | 71.4 | NO | — | — | |
| 13.6 | 18.2 | 0.91 | 68.2 | NO | — | — | |
| 13.0 | 21.7 | 0.87 | 65.2 | NO | — | — | |
| 20.0 | 10.0 | 1.00 | 69.0 | NO | — | — | |
| 19.0 | 14.3 | 0.95 | 66.7 | NO | — | — | |
| 18.2 | 18.2 | 0.91 | 63.6 | NO | — | — | |
| 17.4 | 21.7 | 0.87 | 60.9 | NO | — | — | |
| 25.0 | 10.0 | 1.00 | 64.0 | NO | — | — | |
| 23.8 | 14.3 | 0.95 | 61.9 | YES | 3.5 | 0.5 | 87.5 |
| 22.7 | 18.2 | 0.91 | 59.1 | YES | 3.5 | 0.5 | 87.5 |
| 21.7 | 21.7 | 0.87 | 56.5 | YES | 3.4 | 0.6 | 85.0 |
| 15.0 | 10.0 | 2.00 | 73.0 | NO | — | — | |
| 14.3 | 14.3 | 1.90 | 69.5 | NO | — | — | |
| 13.6 | 18.2 | 1.82 | 66.4 | YES | 3.4 | 0.6 | 85.0 |

TABLE 4-continued

Formulations parameters that lead to Biphasic product formations as indicated in the phase separation column.

| % Total Surfactant | % MD 180 | % MgSO4 | % Water | Phase Separation | Top (cm) | Bottom (cm) | % Top Layer |
|---|---|---|---|---|---|---|---|
| 13.0 | 21.7 | 1.74 | 63.5 | YES | 2.1 | 1.9 | 52.5 |
| 20.0 | 10.0 | 2.00 | 68.0 | NO | — | — | |
| 19.0 | 14.3 | 1.90 | 64.8 | YES | 3.0 | 1.0 | 75.0 |
| 18.2 | 18.2 | 1.82 | 61.8 | YES | 2.8 | 1.2 | 70.0 |
| 17.4 | 21.7 | 1.74 | 59.1 | YES | 2.7 | 1.3 | 67.5 |
| 25.0 | 10.0 | 2.00 | 63.0 | YES | 3.7 | 0.3 | 92.5 |
| 23.8 | 14.3 | 1.90 | 60.0 | NO | — | — | |
| 22.7 | 18.2 | 1.82 | 57.3 | YES | 3.6 | 0.4 | 90.0 |
| 21.7 | 21.7 | 1.74 | 54.8 | YES | 3.0 | 1.0 | 75.0 |
| 15.0 | 10.0 | 3.00 | 72.0 | YES | 3.5 | 0.5 | 87.5 |
| 14.3 | 14.3 | 2.86 | 68.6 | YES | 2.8 | 1.2 | 70.0 |
| 13.6 | 18.2 | 2.73 | 65.5 | YES | 2.2 | 1.8 | 55.0 |
| 13.0 | 21.7 | 2.61 | 62.6 | YES | 1.8 | 2.2 | 45.0 |
| 20.0 | 10 | 3.00 | 67.0 | YES | 3.5 | 0.5 | 87.5 |
| 19.0 | 14.29 | 2.86 | 63.8 | YES | 2.9 | 1.1 | 72.5 |
| 18.2 | 18.18 | 2.73 | 60.9 | YES | 3.3 | 0.7 | 82.5 |
| 17.4 | 21.74 | 2.61 | 58.3 | YES | 2.2 | 1.8 | 55.0 |
| 25.0 | 10 | 3.00 | 62.0 | NO | — | — | |
| 23.8 | 14.29 | 2.86 | 59.0 | NO | — | — | |
| 22.7 | 18.18 | 2.73 | 56.4 | YES | 2.2 | 1.4 | 61.1 |
| 21.7 | 21.74 | 2.61 | 53.9 | YES | 2.8 | 1.2 | 70.0 |
| 15.0 | 0.00 | 0 | 85.0 | NO | — | — | |
| 13.6 | 9.09 | 0 | 77.3 | NO | — | — | |
| 13.0 | 13.04 | 0 | 73.9 | NO | — | — | |
| 12.5 | 16.67 | 0 | 70.8 | NO | — | — | |
| 12.0 | 20.00 | 0 | 68.0 | NO | — | — | |
| 10.7 | 28.57 | 0 | 60.7 | NO | — | — | |
| 20.0 | 0.00 | 0 | 80.0 | NO | — | — | |
| 18.2 | 9.09 | 0 | 72.7 | NO | — | — | |
| 17.4 | 13.04 | 0 | 69.6 | NO | — | — | |
| 16.7 | 16.67 | 0 | 66.7 | NO | — | — | |
| 16.0 | 20.00 | 0 | 64.0 | YES | 3.5 | 0.5 | 87.5 |
| 14.3 | 28.57 | 0 | 57.1 | YES | 3.1 | 0.9 | 77.5 |
| 13.8 | 31.03 | 0 | 55.2 | YES | 3.1 | 0.9 | 77.5 |
| 13.3 | 33.33 | 0 | 53.3 | YES | 3.1 | 0.9 | 77.5 |
| 12.5 | 37.50 | 0 | 50.0 | YES | 3.0 | 1.0 | 75.0 |
| 11.8 | 41.18 | 0 | 47.1 | NO | — | — | |
| 25.0 | 0.00 | 0 | 75.0 | NO | — | — | |
| 22.7 | 9.09 | 0 | 68.2 | NO | — | — | |
| 21.7 | 13.04 | 0 | 65.2 | NO | — | — | |
| 20.8 | 16.67 | 0 | 62.5 | NO | — | — | |
| 20.0 | 20.00 | 0 | 60.0 | YES | 3.6 | 0.4 | 90.0 |
| 19.2 | 23.08 | 0 | 57.7 | YES | 3.2 | 0.8 | 80.0 |
| 30.0 | 0.00 | 0 | 70.0 | NO | — | — | |
| 27.3 | 9.09 | 0 | 63.6 | NO | — | — | |
| 26.1 | 13.04 | 0 | 60.9 | NO | — | — | |
| 25.0 | 16.67 | 0 | 58.3 | NO | — | — | |
| 24.0 | 20.00 | 0 | 56.0 | YES | 3.2 | 0.8 | 80.0 |
| 23.1 | 23.08 | 0 | 53.8 | YES | 3.2 | 0.8 | 80.0 |
| 22.2 | 25.93 | 0 | 51.9 | YES | 3.0 | 1.0 | 75.0 |
| 21.4 | 28.57 | 0 | 50.0 | YES | 3.0 | 1.0 | 75.0 |
| 20.0 | 33.33 | 0 | 46.7 | YES | 3.0 | 1.0 | 75.0 |
| 18.8 | 37.50 | 0 | 43.8 | YES | 2.8 | 1.2 | 70.0 |
| 17.6 | 41.18 | 0 | 41.2 | YES | 2.8 | 1.2 | 70.0 |
| 10.0 | 30.00 | 0 | 60.0 | NO | — | — | |
| 9.5 | 33.33 | 0 | 57.1 | NO | — | — | |
| 20.0 | 30.00 | 0 | 50.0 | YES | 3.0 | 1.0 | 75.0 |
| 19.0 | 33.33 | 0 | 47.6 | YES | 3.0 | 1.0 | 75.0 |
| 18.2 | 36.36 | 0 | 45.5 | YES | 2.8 | 1.2 | 70.0 |
| 17.4 | 39.13 | 0 | 43.5 | YES | 2.8 | 1.2 | 70.0 |
| 16.7 | 41.67 | 0 | 41.7 | YES | 2.4 | 1.6 | 60.0 |
| 15.4 | 46.15 | 0 | 38.5 | YES | 2.4 | 1.6 | 60.0 |
| 14.3 | 50.00 | 0 | 35.7 | YES | 2.5 | 1.5 | 62.5 |
| 30.0 | 20.00 | 0 | 50.0 | YES | 3.0 | 1.0 | 75.0 |
| 28.6 | 23.81 | 0 | 47.6 | YES | 3.0 | 1.0 | 75.0 |
| 27.3 | 27.27 | 0 | 45.5 | YES | 2.8 | 1.2 | 70.0 |
| 26.1 | 30.43 | 0 | 43.5 | YES | 2.8 | 1.2 | 70.0 |

Example 16

In this example, applicants prepared samples comprising 2:1 ratio of sodium lauryl ether sulfate to cocoamidopropyl betaine (SLES/CAPB) as surfactant; maltodextrin and glycerol. Applicants then compared the viscosity of the samples undiluted to the viscosity of same samples when diluted (sample to water). Measurements were taken at dilution ratio of 2 to 1.

Results are set forth in Table below.

TABLE 5

Comparison of the viscosity of the SLES/CAPB (2:1) - MD 180 samples before and after dilution

| sample | | | | Original | | | 2:1 dilution | | |
| --- | --- | --- | --- | --- | --- | --- | --- | --- | --- |
| Surf % | MD % | Water | glycerol % | 1 s-1 | 10 s-1 | 100 s-1 | 1 s-1 | 10 s-1 | 100 s-1 |
| 10 | 60 | 30 | 0 | 12,230 | 8,300 | 3,490 | 55,220 | 10,560 | 1,069 |
| 15 | 50 | 35 | 0 | 11,600 | 4,400 | 2,700 | 171,460 | 13,480 | 1,880 |
| 20 | 50 | 30 | 0 | 37,600 | 12,350 | 3,800 | 221,678 | 16,480 | 2,230 |
| 25 | 40 | 35 | 0 | 25,634 | 7,933 | 21 | 551,097 | 53,360 | 6,220 |
| 30 | 40 | 30 | 0 | 27,088 | 5,849 | 520 | 204,650 | 31,754 | 3,360 |
| 20 | 40 | 35 | 5 | 11,435 | 6,848 | 1,315 | 193,037 | 17,196 | 2,065 |

The mechanism for the dilution thickening observed in the Table is believed to be explained by the phase behavior. Specifically, the original two-layer (biphasic) formulation is believed to exhibit relatively low viscosity due to existence of dispersed phase in the continuous phase. That is, typically, the viscosity is low enough so that the disperse phase separates from the continuous phase to form two layer product (biphasic). Upon dilution, the sample is believed to approach isotropic solution phase (two-phase to one-one phase boundary) and viscosity is believed to increase due to existence of rod-like surfactant micelles and decreasing amount of dispersed phase. The viscosity is believed to reach maximum at boundary of the isotropic phase. Further dilution with water is believed to break the rod-like micelle into spherical micelle leading to water-like viscosity. Dilution thickening phenomenon may occur within a wide range of surfactant and polysaccharide concentrations and can occur with or without salt.

FIG. 1 is a graph showing changes in viscosity (measured at shear rate $10S^{-1}$) of the formulation upon dilution in water.

Example 17

Table 6 listed three formulations of SLES/CAPB—MD 180 combination. According to the phase diagram shown in FIG. 2, all three formulations are in the bi-layer region that the formulation visibly separates into two layers. As shown in FIG. 3, which measures the viscosity of the formulation upon dilution (routes shown in FIG. 2), all three formulations' original viscosity starts low. However, the viscosity starts to increase dramatically as the MD 180 concentration (sugar) approaches the phase separation boundary. This increase in viscosity is an indication of the formation of the rod-like micelles in the solution. Further dilution of the formulations leads to very low viscosity again. The same rheology behavior was generally observed along phase separation boundary for all the surfactant concentrations examined. Therefore, based on these observations, it can be hypothesized that, with the addition of MD 180 and the decrease of the water content in the system, surfactant aggregates change shape from spherical to rod; and that, due to the high efficiency of the rod-like micelle in terms of causing depletion induced phase separation, the surfactant/MD 180/water mixture separated into two phases as a consequence.

TABLE 6

Figure 2:
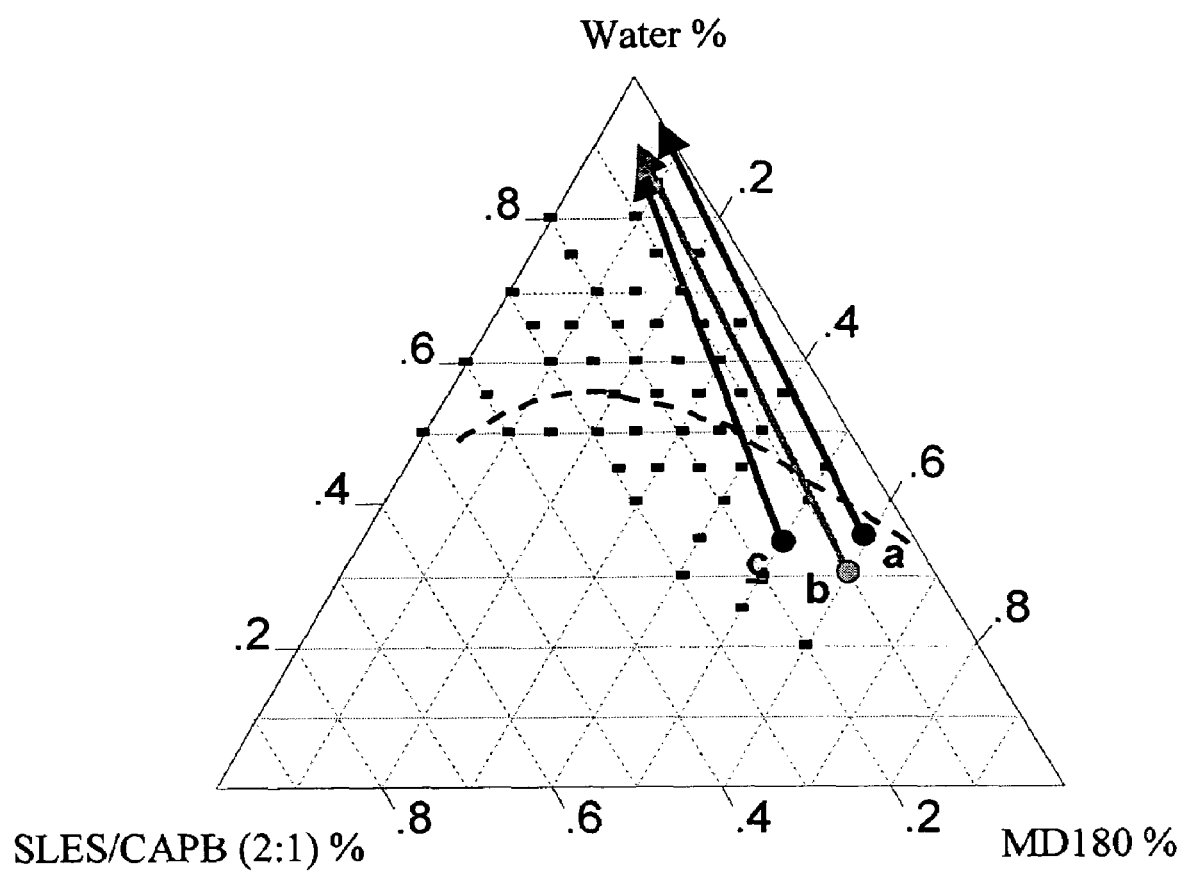
FIG. 2 is the phase diagram of SLES/CAPB (2:1)—MD 180—Water at room temperature. The dashed black line is the boundary between the one-layer product and the two-layer product. Three arrow lines (colored as blue, green and red) are the dilution routes of formulations, a, b and c in the space of phase diagram, respectively.
Figure 3:
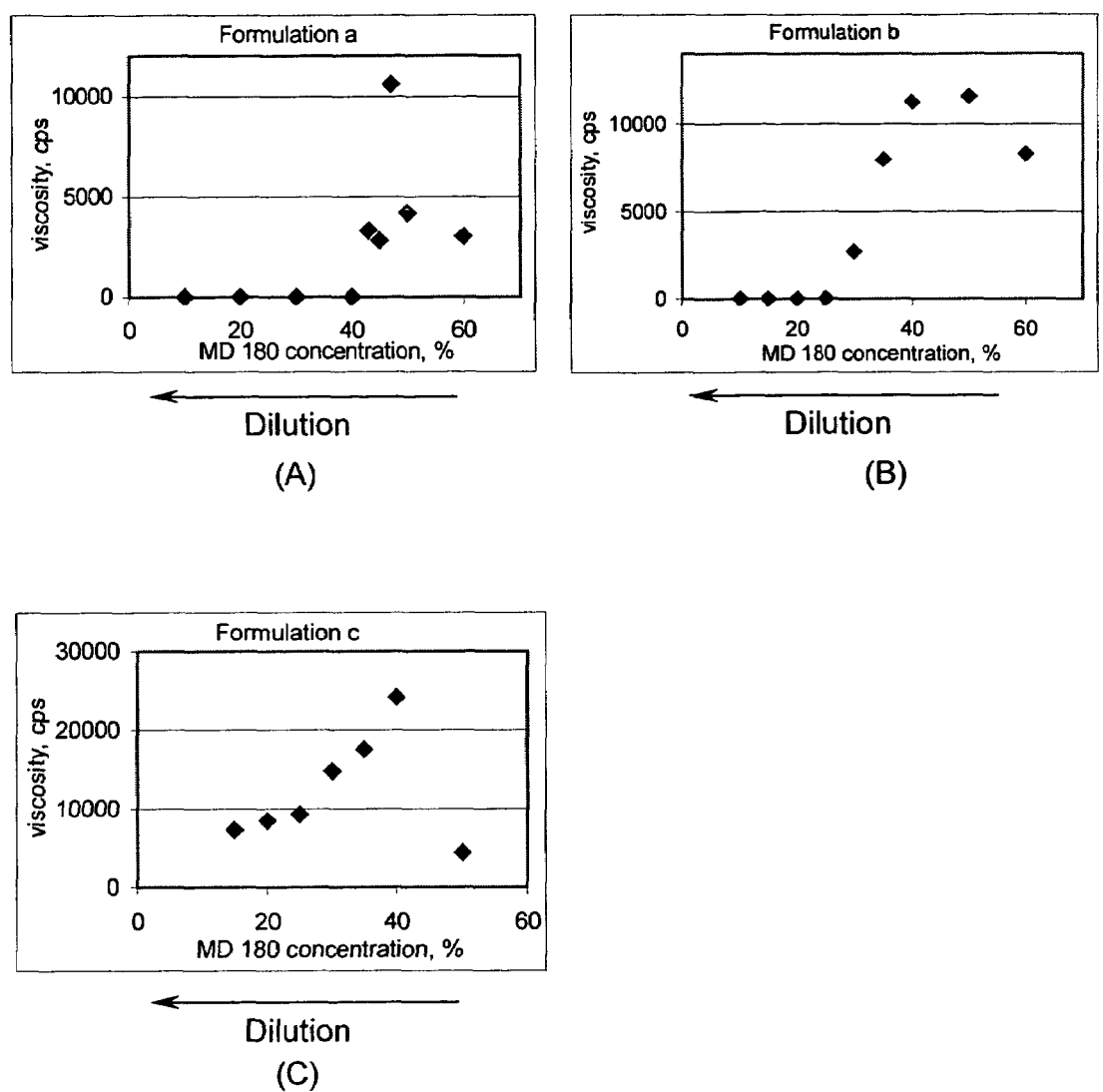
FIG. 3 is the viscosity (at shear rate $10s^{-1}$) change of the formulations a (Figure A), b (Figure B) and c (Figure C) as they dilute along the routes indicated in FIG. 2.

Composition of formulations a, b and c in FIG. 2.

| Formulation | SLES/CAPB | MD 180 | Water |
| --- | --- | --- | --- |
| a | 5 | 60 | 35 |
| b | 10 | 60 | 30 |
| c | 15 | 50 | 35 |

*MD 180 is maltodextrin having dextrose equivalent of about 18, degree of polymerization of 6.2 and average molecular weight of about 1000.

The invention claimed is:

1. A method for enhancing the viscosity of a composition when said composition is diluted with water relative to undiluted sample of the same composition (dilution thickening) while using 3% or less salt to provide said dilution thickening, wherein said process comprises
   (1) preparing a composition which comprises:
      (a) 5% to 75% by wt. of a surfactant selected from the group consisting of anionic surfactants, nonionic surfactants, amphoteric/zwitterionic surfactants, cationic surfactants and mixtures thereof;
      (b) at least 15%, by wt. of polydextrose or mixture of polydextrose molecules, wherein the degree of polymerization (e.g., number of linking glucose units) is 4 to 22 (this corresponds to MW of about 600 to about 3600); and
      (c) balance water and minors; wherein said composition exhibits phase separation upon preparation to form a biphasic liquid; and
   (2) diluting said biphasic liquid with water such that the viscosity of the diluted composition, when measured at shear ratio of $10s^{-1}$ at dilution of 2:1, is thicker than the viscosity of the undiluted composition.

2. A method according to claim 1, wherein 2% or less salt is used.

3. A method according to claim 1, wherein the ratio of water to composition used to provide the dilution thickening effect ranges from 25:75 to 75:25.

* * * * *